(12) United States Patent
Stauffer

(10) Patent No.: US 9,079,849 B2
(45) Date of Patent: Jul. 14, 2015

(54) SYNTHESIS OF METAL ALKOXIDES

(71) Applicant: John E. Stauffer, Greenwich, CT (US)

(72) Inventor: John E. Stauffer, Greenwich, CT (US)

( * ) Notice: Subject to any disclaimer, the term of this patent is extended or adjusted under 35 U.S.C. 154(b) by 157 days.

(21) Appl. No.: 13/889,399

(22) Filed: May 8, 2013

(65) Prior Publication Data

US 2014/0336406 A1  Nov. 13, 2014

(51) Int. Cl.
| | |
|---|---|
| *C07F 7/28* | (2006.01) |
| *C07F 7/02* | (2006.01) |
| *C07C 67/08* | (2006.01) |
| *C07F 7/00* | (2006.01) |
| *C07C 17/00* | (2006.01) |
| *C07F 7/18* | (2006.01) |

(52) U.S. Cl.
CPC ............... *C07C 67/08* (2013.01); *C07C 17/00* (2013.01); *C07F 7/00* (2013.01); *C07F 7/188* (2013.01); *C07F 7/28* (2013.01)

(58) Field of Classification Search
CPC .............. C07C 67/08; C07F 7/04; C07F 7/28
See application file for complete search history.

(56) References Cited

U.S. PATENT DOCUMENTS 5,557,001 A * 9/1996 Stauffer ................. 556/470

OTHER PUBLICATIONS

Zaragoza Dorwald, Side Reactions in Organic Synthesis, 2005, Wiley-VCH Verlag GmbH & Co. KGaA, Weinheim, Preface. p. IX.*

* cited by examiner

*Primary Examiner* — Paul A Zucker
(74) *Attorney, Agent, or Firm* — Young Basile Hanlon & MacFarlane, P.C.

(57) ABSTRACT

A process for preparing metal alkoxides starting with a metal chloride and esters of either succinic acid or glutaric acid to produce metal alkoxide, an acid anhydride and alkyl chloride. Esterification of the acid anhydride with alcohol regenerates the ester of organic acid. The first step is carried out under anhydrous conditions. By regenerating the organic acid esters in the process, the only byproduct is an alkyl chloride.

10 Claims, 1 Drawing Sheet

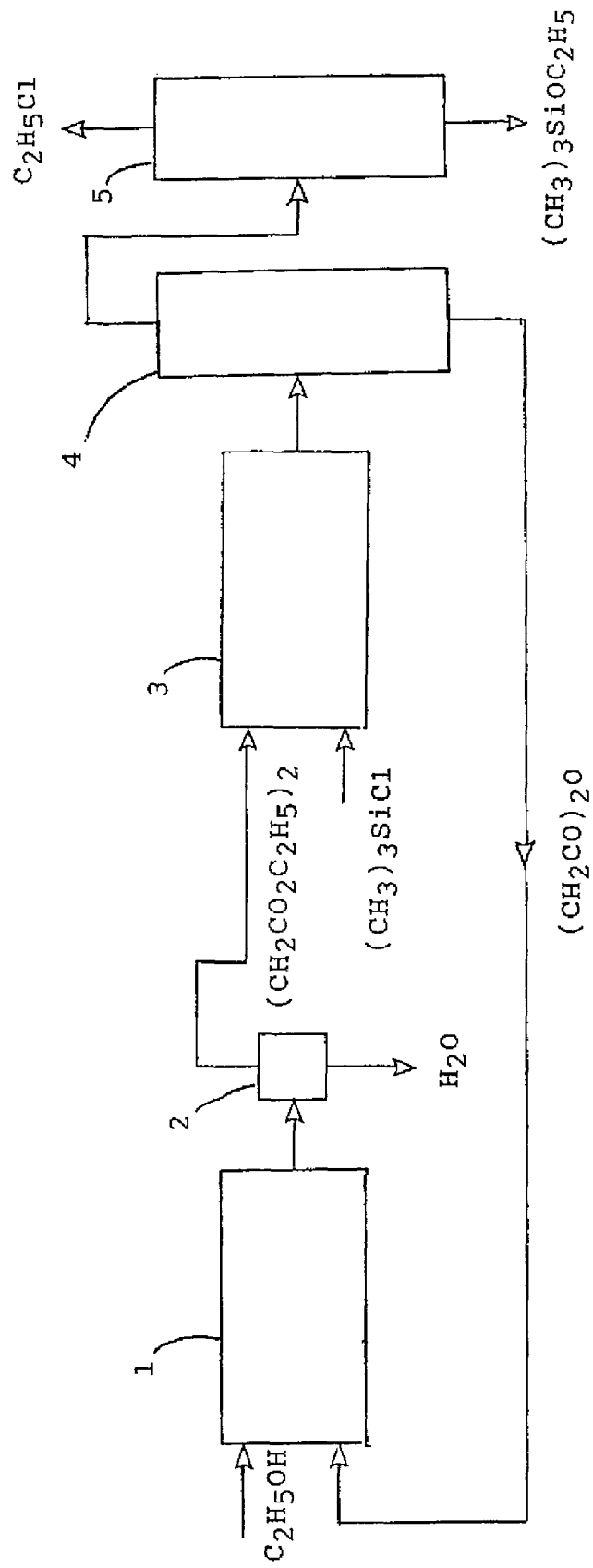

SYNTHESIS OF METAL ALKOXIDES

FIELD OF THE INVENTION

A process is provided for the preparation of metal alkoxides from the corresponding metal chlorides and alcohols.

BACKGROUND OF THE INVENTION

The standard method of preparing metal alkoxides is by the direct reaction of a metal chloride with alcohol to provide the desired alkoxide and hydrogen chloride. A good example of this procedure is the reaction of titanium tetrachloride with methyl alcohol to give dichlorotitanium methoxide and hydrogen chloride. In a similar manner the alkoxides of zirconium, columbium, vanadium and molybdenum have been prepared.

This method of producing alkoxides has certain limitations. The most notable drawback is that complete substitution of the chlorine atoms cannot be achieved. In order to prepare a fully substituted alkoxide, the partially substituted alkoxide must be treated with a base, for example, sodium ethoxide.

A further disadvantage of existing technology is that the synthesis generates hydrogen chloride. Under these conditions a secondary reaction can occur between the hydrogen chloride and alcohol forming an alkyl chloride and water. Several methods of suppressing this side reaction are reported. In addition, various attempts using engineering principles have been tried to circumvent the problem.

SUMMARY OF THE INVENTION

A process is provided for preparing metal alkoxides including those of silicon and titanium. The process starts by reacting the corresponding metal chloride with an ester of succinic acid or glutaric acid to generate the desired metal alkoxide, acid anhydride and an alkyl chloride. This reaction is conducted in the vapor phase over a heterogeneous catalyst at a temperature in the range of 200° to 275° C. and a pressure close to one atmosphere. The effective catalyst is selected from the group consisting of aluminum oxide and silica gel.

The esters of succinic acid or glutaric acid are regenerated by reacting the acid anhydride from the first reaction with alcohol. Before recycling the esters, water is removed so that the first reaction is maintained under anhydrous conditions.

Purified product is obtained by a series of distillations to separate the acid anhydride and byproduct alkyl chloride. In addition, various substituted alkoxides can be isolated from each other due to the differences in the boiling points.

BRIEF SUMMARY OF THE DRAWINGS

The description herein makes reference to the accompanying single drawing FIGURE showing a preferred embodiment of the process with principal pieces of equipment and product streams illustrated in block diagram.

DETAILED DESCRIPTION OF THE ILLUSTRATIVE EMBODIMENT

The present invention covers the preparation of metal alkoxides from the corresponding metal chloride and a given alcohol. A key feature of the process is that the primary or esterification step is carried out under anhydrous conditions. Water is excluded from this reaction. Only during the secondary or regenerative step is water present.

The significance of the anhydrous conditions is severalfold. First, because there is no moisture present, neither the metal chloride nor the resulting ester can react to form oligomers and sludges of various compositions. Second, in the absence of hydrochloric acid, the selection of materials of construction is simplified. Corrosion resistant materials are not required. Third, there is no waste hydrogen chloride to treat or otherwise dispose of. And fourthly, the byproduct alkyl chloride can easily be recovered and used in organic synthesis.

Anhydrous conditions are achieved in the esterification step by the use of esters of succinic acid or glutaric acid as reagents. For example, diethyl succinate can be used to esterify a metal chloride. Because ethyl chloride is formed in this case instead of hydrogen chloride, the reaction between hydrogen chloride and an alcohol to form water is avoided.

A better insight of the present invention can be gained by looking at a specific application. Thus, in the preparation of a silicone monomer, trimethyl chlorosilane is reacted with diethyl succinate to give trimethyl ethoxy silane, succinic anhydride, and ethyl chloride as follows:

$$(CH_3)_3SiCl + (CH_2CO_2C_2H_5)_2 \rightarrow (CH_3)_3SiOC_2H_5 + (CH_2CO)_2O + C_2H_5Cl \qquad 1.$$

In a second step, isolated from the first reaction, diethyl succinate is regenerated by reacting succinic anhydride with ethyl alcohol to form diethyl succinate and water as follows:

$$(CH_2CO)_2O + 2C_2H_5OH \rightarrow (CH_2CO_2C_2H_5)_2 + H_2O \qquad 2.$$

When the above two equations are combined, the result represents the overall reaction for the process as shown below:

$$(CH_3)_3SiCl + 2C_2H_5OH \rightarrow (CH_3)_3SiOC_2H_5 + C_2H_5Cl + H_2O \qquad 3.$$

It should be noted that there is no net consumption of succinic acid in the process.

A key feature of the present invention is the use of esters of succinic acid or glutaric acid as the case may be. The feasibility of this approach is best appreciated by examining the mechanism of the esterification reaction shown by equation 1. This equation can be considered to be the summation of the following reactions:

$$(CH_3)_3SiCl + C_2H_5OH \rightarrow (CH_3)_3SiOC_2H_5 + HCl \qquad 4.$$

$$HCl + C_2H_5OH \rightarrow C_2H_5Cl + H_2O \qquad 5.$$

$$(CH_2CO_2C_2H_5)_2 + 2H_2O \rightarrow (CH_2CO_2H)_2 + 2C_2H_5OH \qquad 6.$$

$$(CH_2CO_2H)_2 \rightarrow (CH_2CO)_2O + H_2O \qquad 7.$$

Equation 4 is a variation of Ebelman's classic synthesis for silicon esters. It goes to completion under standard operating conditions of temperature and pressure. The reaction shown by equation 5 is reversible in the range of 25° to 275° C. and is promoted by such catalysts as aluminum oxide and salts of copper and zinc.

The hydrolysis reaction of equation 6 is the opposite of a straightforward esterification synthesis. It is reversible and is promoted by a catalyst as well as by elevated temperatures. Effective catalysts include alumina and silica gel.

Equation 7 shows the dehydration of succinic acid to succinic anhydride. This reaction is favored by heating and/or the removal of water. The dehydration reaction is especially significant because the anhydride formed is a ring compound. Succinic anhydride has the structure of a ring containing five atoms whereas glutaric anhydride has the shape of a ring with six atoms. Because organic chemistry favors the formation of ring compounds with five or six atoms in the ring, the reaction shown by equation 7 is facilitated.

Taking the requirements for the reactions shown by equations 4-7 into consideration, the conditions for the reaction of equation 1 can be determined. Since dimethyl succinate has a boiling point of 195.9° C., it is contemplated to conduct the esterification reaction of equation 1 in the vapor phase at a temperature in the range of 200° to 275° C. and close to 1 atmosphere. A heterogeneous catalyst comprising alumina or silica gel is recommended with or without zinc.

Step 2 of the present invention, shown by equation 2, is the classical synthesis for the production of organic esters. Acid anhydrides are more reactive than organic acids so the esterification process of the present invention proceeds more rapidly.

The present invention has been described for the preparation of silicone monomers, however, the technology is more general in its application. For example, titanium chlorides undergo the same esterification reactions as silicon chlorides. Thus, dichlorotitanium methoxide can be prepared. This is an interesting compound for such uses as catalysts and ceramics.

The process of the present invention can be better visualized by referring to FIG. 1. This FIGURE shows a block diagram with the major pieces of equipment employed. In reactor 1, succinic anhydride is reacted with alcohol, in this case ethyl alcohol, to produce diethyl succinate and water. After the water is removed in separator 2, the ester is fed to reactor 3 along with chlorosilane. This second reactor of shell and tube design contains the catalyst required for the esterification reaction. Exit gases from reactor 3 are sent to distillation column 4 where succinic anhydride is removed. Silicon ethoxide is separated from ethyl chloride in distillation column 5. Additional distillation may be utilized in equipment not shown to produce a product of desired purity.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for preparing a metal alkoxide of silicon comprising the steps of:
    (a) reacting a silicon chloride with an ester of succinic acid or glutaric acid in the presence of a catalyst selected from the group consisting of alumina oxide and silica gel to produce the metal alkoxide of silicon, an acid anhydride and an alkyl chloride; and
    (b) esterifying the acid anhydride produced in step (a) with alcohol to regenerate the ester of succinic acid or glutaric acid.

2. A process according to claim 1 in which step (a) is carried out under anhydrous conditions.

3. A process according to claim 1 wherein step (a) is carried out in the vapor phase over a catalyst.

4. A process according to claim 3 wherein step (a) is carried out at a temperature in the range of about 200° to 275° C. and at a pressure of about 1 ATM.

5. A process according to claim 1, wherein the ester of succinic acid is dimethyl succinate.

6. A process according to claim 1, further comprising the steps of:
    (c) removing water produced during step (b); and
    (d) recycling the ester of succinic acid or glutaric acid.

7. A process for preparing a metal alkoxide of titanium comprising the steps of:
    (a) reacting a titanium chloride with an ester of succinic acid or glutaric acid in the presence of a catalyst selected from the group consisting of alumina oxide and silica gel to produce the metal alkoxide of titanium, an acid anhydride and an alkyl chloride; and
    (b) esterifying the acid anhydride produced in step (a) with alcohol to regenerate the ester of succinic acid or glutaric acid.

8. A process according to claim 7 in which step (a) is carried out under anhydrous conditions.

9. A process according to claim 7 wherein step (a) is carried out in the vapor phase over a catalyst.

10. A process according to claim 9 wherein step (a) is carried out at a temperature in the range of about 200° to 275° C. and at a pressure of about 1 ATM.

\* \* \* \* \*